United States Patent
Wang et al.

(10) Patent No.: US 7,664,541 B2
(45) Date of Patent: Feb. 16, 2010

(54) MULTI-CHANNEL MAGNETIC RESONANCE IMAGING RECONSTRUCTION METHOD FOR WATER-FAT SEPARATION

(75) Inventors: Jian Min Wang, Shenzhen (CN); De He Weng, Shenzhen (CN)

(73) Assignee: Siemens Aktiengesellschaft, Munich (DE)

( * ) Notice: Subject to any disclaimer, the term of this patent is extended or adjusted under 35 U.S.C. 154(b) by 902 days.

(21) Appl. No.: 11/363,918

(22) Filed: Feb. 28, 2006

(65) Prior Publication Data

US 2006/0241381 A1    Oct. 26, 2006

(30) Foreign Application Priority Data

Feb. 28, 2005    (CN) .................... 2005 1 0008973

(51) Int. Cl.
*A61B 5/05*    (2006.01)
*G01V 3/00*    (2006.01)

(52) U.S. Cl. .................... 600/410; 324/309; 324/307

(58) Field of Classification Search .................... 600/410
See application file for complete search history.

(56) References Cited

U.S. PATENT DOCUMENTS

| | | | | |
|---|---|---|---|---|
| 6,466,014 B1* | 10/2002 | Ma | .................... | 324/307 |
| 7,227,359 B2* | 6/2007 | Ma | .................... | 324/309 |
| 7,358,729 B2* | 4/2008 | Ma et al. | .................... | 324/307 |
| 2003/0060697 A1* | 3/2003 | Zhang et al. | .................... | 600/410 |
| 2005/0168221 A1* | 8/2005 | Miyoshi | .................... | 324/309 |

* cited by examiner

*Primary Examiner*—Long V Le
*Assistant Examiner*—Hien Nguyen
(74) *Attorney, Agent, or Firm*—Schiff Hardin LLP

(57) ABSTRACT

In a multi-channel magnetic resonance imaging reconstruction method for water-fat separation, one in-phase image and two opposed-phase images are acquired with multiple reception coils in respective channels. The sensitivity distribution of the coils of the respective channels is calculated. The images of respective channels are merged dependent on the sensitivity distribution. A phase difference between the two opposed-phase images is calculated. At lease one characteristic region of the in-phase image is detected, which is used as a criterion for phase correction. The phases of the opposed-phase images are corrected and images of water and fat are calculated. The method provides stable and reliable imaging, has a short reconstruction time and also solves the problem that images of water and fat may be exchanged.

12 Claims, 1 Drawing Sheet

MULTI-CHANNEL MAGNETIC RESONANCE IMAGING RECONSTRUCTION METHOD FOR WATER-FAT SEPARATION

BACKGROUND OF THE INVENTION

1. Field of the Invention

The present invention relates to a multi-channel magnetic resonance imaging reconstruction method for water-fat separation, and more particularly to a Dixon method-based multi-channel magnetic resonance imaging reconstruction method for water-fat separation.

2. Description of the Prior Art

In magnetic resonance imaging (MRI), hydrogen protons in adipose tissues and hydrogen protons in other tissues of the human body have different resonance frequencies because they are in a different molecular environment. Also, after hydrogen protons in adipose tissues and other tissues are simultaneously excited by radio frequency pulses they have different relaxation times. Signals collected for adipose tissues and non-adipose tissues in various echo times have different signal strength.

The Dixon method is a method used in MRI for producing an image of pure water protons, the basic principle of which is: collecting, respectively, both in-phase and opposed-phase echo signals of protons in water and fat, and performing calculations on the signals of the two different phases to remove the fat signal, producing an image of pure water protons and thus achieving fat suppression. The Dixon method has disadvantages in that it is affected, to a relatively large extent, by non-uniformity of magnetic field, exposed to respiratory movements, and based on a complex calculation technique that is subject to errors.

An improved three-point Dixon method has been widely used so as to obtain images of water and fat at one time, and the principle thereof is: acquiring one in-phase image and two opposed-phase images and at the same time, calculating an additional phase caused by non-uniformity of the magnetic field from the two opposed-phase images, performing phase correction on the two opposed-phase images, and then using the two opposed-phase images together with the in-phase image to obtain images of water and fat.

The disadvantages of the three-point Dixon method lie in that the additional phase calculated from the two opposed-phase images can not be directly used to perform phase correction on the images, for the fact that the additional phase due to non-uniformity of magnetic field may exceed, that is to say, phase wrapping occurs and therefore there is a need for performing phase unwrapping. However, phase unwrapping is mathematically a problem without a solution, and in water-fat separation techniques, in order to perform phase unwrapping, it is assumed that the spatial change in non-uniformity of the magnetic field is slow, so the calculation process of phase unwrapping is quite time-consuming.

When multi-channel coils are used for imaging, in order to obtain merged images of water and fat, images of water and fat of respective channels are calculated respectively, that is to say, for each of the channels, the two opposed-phase images calculated are used to calculate the additional phase caused by the non-uniform magnetic field to perform phase unwrapping, the unwrapped phase is used to perform phase correction on the two opposed-phase images, and finally, images of water and fat are obtained; and then the images of water of respective channels and the images of fat of respective channels are merged, respectively, to obtain the final result.

The above-described scheme has several problems, as follows:

(1) reconstruction time is too long;

(2) for channels which have a poor image signal-to-noise ratio (SNR), images of water and fat obtained are unreliable; and (3) due to inherent instability of phase unwrapping, for some channels, the images of water and fat calculated may be exchanged, causing errors in the merged images of water and fat.

Due to the inherent disadvantages of phase unwrapping, a new scheme has been proposed: collecting three images of 0, $\pi/2$, $\pi$ finding, from the three images, direction vectors representative of fat and water signals and based on physical characteristics thereof, determining the correct solutions, then calculating a phase difference caused by the non-uniform field from the vectors of fat and water signals to correct the phase difference between the latter two images, and calculating images of water and fat.

However, this procedure also has several problems, as follows:

(1) since signals of respective channels must be processed respectively, reconstruction time is long; and (2) for channels or regions which have a poor image SNR, the images of water and fat obtained are unreliable and the merged images of water and fat derived therefrom are unreliable as well.

Therefore, the inability to provide a Dixon method-based multi-channel reconstruction method for water-fat separation that eliminates the problem of reconstructing images of water and fat that are unstable and that take a long time is a problem in MRI technology in need of a solution.

SUMMARY OF THE INVENTION

An object of the present invention is to provide a multi-channel magnetic resonance imaging reconstruction method for water-fat separation, which yields stable and reliable imaging and has a short reconstruction time.

Another object of the present invention is to provide a multi-channel magnetic resonance imaging reconstruction method for water-fat separation, which has an optimized SNR for the phase unwrapping image.

Yet another object of the present invention is to provide a multi-channel magnetic resonance imaging reconstruction method for water-fat separation, which avoids the problem of images of water and fat being subject to exchange in water-fat separation reconstruction.

The above objects are achieved in accordance with the present invention by a multi-channel magnetic resonance imaging reconstruction method for water-fat separation including the following steps:

(i) acquiring one in-phase image and two opposed-phase images using multiple reception coils in respective channels;

(ii) calculating the sensitivity distribution of the coils of the respective channels;

(iii) merging the images of respective channels on the basis of the sensitivity distribution;

(iv) calculating a phase difference between the two opposed-phase images;

(v) detecting at least one characteristic region of the in-phase image, which is used as a criterion for phase correction; and (vi) correcting phases of the merged opposed-phase images and calculating images of water and fat therefrom.

Step (ii) can further involve calculating the sum of squares of moduli of the in-phase images of respective channels, which is then extracted; selecting a channel signal having a relatively high SNR among the in-phase images or a linear combination of respective channel signals and normalizing the modulus thereof; and, calculating the sensitivity distribution of coils of respective channels.

In another embodiment of the multi-channel magnetic resonance imaging reconstruction method for water-fat separation according to the present invention, step (ii) also can utilize a corrected spatially-matched filter method to calculate the sensitivity distribution of coils of respective channels, that is, signals of each pixel and its neighborhood of images of respective channels are used to calculate the signal and noise correlation matrix, and the sensitivity distribution of coils of respective channels is derived by calculating the characteristic value and characteristic vector of the signal correlation matrix.

In step (iii), the images of respective channels are merged to obtain merged images having an optimized SNR, and at the same time, phases of the images are reserved.

In step (iv), a phase unwrapping method is used to perform phase unwrapping on the phase difference to obtain a corrected phase.

In said step (v), use is made of the fact that in most images the fat signal is relatively high to detect fat of the image, or an edge detection method is used to detect subcutaneous fat, and these fat points are used as a criterion to correct the phase.

The multi-channel magnetic resonance imaging reconstruction method for water-fat separation according to the present invention merges images first, and instead of using common modular merging, the images are merged on the basis of complex techniques. The resulting images not only have an optimized SNR but also reserve what is of most importance in the Dixon method, the phase information, and the result obtained after using the merged images to calculate the phase reflecting non-uniformity of field to perform phase unwrapping has significantly-improved reliability.

In the multi-channel magnetic resonance imaging reconstruction method for water-fat separation according to the present invention, calculation of the images of water and fat is only performed using the merged images, and phase unwrapping is performed only once regardless of the number of channels. Thus, for Dixon imaging of a multi-channel system, much time can be saved.

The multi-channel magnetic resonance imaging reconstruction method for water-fat separation according to the present invention utilizes the merged images to calculate images of water and fat, which is similar to the case of a single channel and capable of obtaining images of pure water and fat, and then by using the criterion of step (v) in the above-described method, the correct images of water and fat can be obtained, thus solving the problem that, due to instability of phase unwrapping methods, offset easily occurs to the result obtained via phase unwrapping, which tends to cause images of water and fat derived from the result to be exchanged.

DESCRIPTION OF THE PREFERRED EMBODIMENTS

Figure 1A:
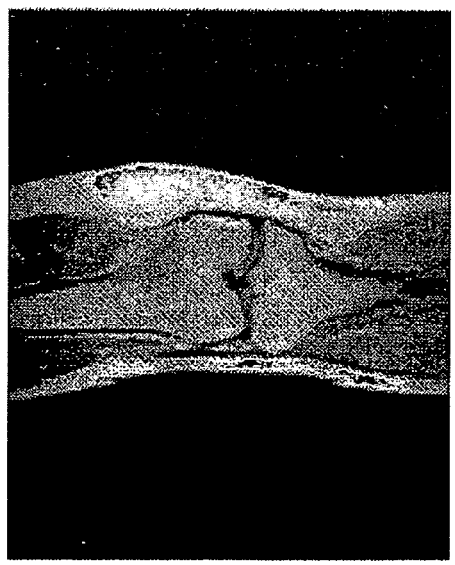
FIG. 1A is an image showing water and fat.

The multi-channel magnetic resonance imaging reconstruction method for water-fat separation according to the present invention includes the following steps:

(i) Acquiring one in-phase image and two opposed-phase images.

It is assumed that $S_0^i(x,y)$, $S_1^i(x,y)$ and $S_2^i(x,y)$ represent the one in-phase image and the two opposed-phase images of channel i, respectively, where i=1 . . . n, and n is the total number of the channels.

(ii) Calculating the sensitivity distribution of coils of respective channels.

This step can be divided into the following steps.

(a) Calculating the sum of squares of moduli of the in-phase images of respective channels, which is then extracted:

$$SOS(x, y) = \sqrt{\sum_{i=1}^{n} |S_0^i(x, y)|^2}$$

(b) Selecting a channel signal having a relatively high SNR $S_0^1(x,y)$ among the in-phase images, and normalizing the modulus thereof:

$$S_0'(x, y) = \frac{S_0^I(x, y)}{|S_0^I(x, y)|}$$

In another embodiment of the present invention, step (b) can be performed by selecting a linear combination of respective channel signals and normalizing the modulus thereof:

$$S_0'(x, y) = \frac{\sum_{i=1}^{n} S_0^i(x, y) \cdot W_i}{\left|\sum_{i=1}^{n} S_0^i(x, y) \cdot W_i\right|},$$

where $W_i$ is weighting.

(c) Calculating the sensitivity distribution of coils of respective channels:

$$P^i(x, y) = \frac{S_0^i(x, y) \cdot [S_0'(x, y)]^*}{SOS(x, y)},$$

where [ ]* represents the conjugate.

The process achieved by steps (a)-(c) of calculating the sensitivity distribution of coils of respective channels also can be performed by other optimization methods, for example, a corrected space matched filter method, that is, signals of each pixel and its neighborhood of images of respective channels are used to calculate the signal and noise correlation matrix, and the sensitivity distribution of coils of respective channels is derived by calculating the characteristic value and characteristic vector of the signal correlation matrix.

(iii) Merging the images of respective channels.

$$S_0(x, y) = \sum_{i=1}^{n} [P^i(x, y)]^* \cdot S_0^i(x, y)$$

$$S_1(x, y) = \sum_{i=1}^{n} [P^i(x, y)]^* \cdot S_1^i(x, y)$$

$$S_2(x, y) = \sum_{i=1}^{n} [P^i(x, y)]^* \cdot S_2^i(x, y)$$

In this step, the images of respective channels are merged to obtain merged images having an optimized SNR, and at the same time, phases of the images are reserved.

(iv) Calculating a phase difference between the two opposed-phase images.

$$\phi(x,y) = \text{angle}[S_2(x,y) \cdot [S_1(x,y)]^*],$$

where angle[ ] represents the operator of calculating phase angle.

A phase unwrapping method is used to perform phase unwrapping on φ(x,y) to obtain a corrected phase φ'(x,y).

(v) Detecting some characteristic regions of the in-phase image, which are used as a criterion for phase correction.

In this step, the fact that in most images the fat signal is relatively high is used to detect fat of said image, or an edge detection method is used to detect subcutaneous fat, and these fat points are used as a criterion to correct the phase φ'(x,y).

(vi) Correcting phases of the opposed-phase images and calculating images of water and fat.

$$I_{water}(x,y) = 0.5 \cdot [S_0(x,y) + 0.5 \cdot (S_1(x,y) \cdot e^{j \cdot 0.5 \cdot \phi'(x,y)} + S_2(x,y) \cdot e^{-j \cdot 0.5 \cdot \phi'(x,y)})]$$

$$I_{fat}(x,y) = 0.5 \cdot [S_0(x,y) - 0.5 \cdot (S_1(x,y) \cdot e^{j \cdot 0.5 \cdot \phi'(x,y)} + S_2(x,y) \cdot e^{-j \cdot 0.5 \cdot \phi'(x,y)})]$$

The multi-channel magnetic resonance imaging reconstruction method for water-fat separation according to the present invention achieves the following objects using the above-described steps (i)-(vi).

(1) Imaging is Stable and Reliable.

In the prior art, phase unwrapping is performed on images of respective channels, respectively. In this case, for channels far away from the field of view (FOV), the received signal is weak and has a poor SNR. A phase derived from an image having a poor SNR will have a poor SNR, and hence, when the calculation of images of water and fat is performed on images of such channels, errors easily occur to phase unwrapping. As a result, the images of water and fat obtained are often wrong in part or completely, eventually causing unreliability of merged images. However, the multi-channel magnetic resonance imaging reconstruction method for water-fat separation according to the present invention merges images first, and instead of by using common modular merging, the images are merged on the basis of complex techniques. The resulting images not only have an optimized SNR but also reserve what is of most importance in the Dixon method, the phase information, and the result obtained by using the merged images to calculate the phase reflecting non-uniformity of field to perform phase unwrapping has significantly-improved reliability.

(2) Reconstruction Time is Short.

In three-point Dixon methods, in order to acquire phase information that correctly reflects a non-uniform field, one must utilize complex phase unwrapping techniques, which is quite time-consuming. In Dixon methods, most of the reconstruction time is occupied by phase unwrapping. Prior art techniques calculate images of water and fat of each channel, respectively, and then perform image merging, and thus, the number of times that phase unwrapping must be performed is equal to the number of channels, so the reconstruction time of prior art techniques is proportional to the number of channels. In the multi-channel magnetic resonance imaging reconstruction method for water-fat separation according to the present invention, the calculation of images of water and fat is only performed on the merged images, and phase unwrapping is performed only once irrespective of the number of channels. Thus, for Dixon imaging of a multi-channel system, much time can be saved.

(3) The Problem that Images of Water and Fat May be Exchanged is Solved.

Due to instability of phase unwrapping methods, it is very easy for the result to offset ±2π, and if such a result is used to calculate images of fat and water, images of water and fat will be exchanged, which is not so severe in the case of a single channel. In the case of multiple channels, however, because prior art reconstruction methods first calculate images of water and fat of each of the channels separately, if, for a part of the channels, images of water and fat obtained are exchanged, images of water and fat obtained via merging will be wrong. The multi-channel magnetic resonance imaging reconstruction method for water-fat separation according to the present invention utilizes the merged images to calculate images of water and fat, which is similar to the case of a single channel that is capable of obtaining images of pure water and fat. By using the criterion of step (v) in the above-described method, the correct images of water and fat can be obtained.

Figure 1B:
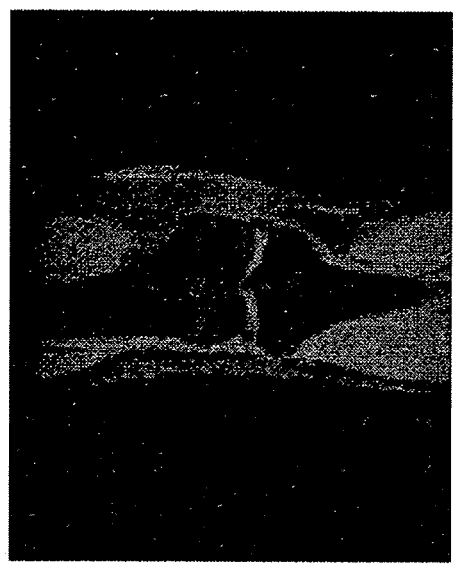
FIG. 1B is an image of the water of FIG. 1A obtained by employing the multi-channel magnetic resonance imaging reconstruction method for water-fat separation according to the present invention.
Figure 1C:
FIG. 1C is an image of the fat of FIG. 1A obtained by employing the multi-channel magnetic resonance imaging reconstruction method for water-fat separation according to the present invention.

Referring to FIGS. 1A-1C, in practical applications of said multi-channel magnetic resonance imaging reconstruction method for water-fat separation according to the present invention, a spin-echo-based Dixon method is employed, and the one in-phase image and two opposed-phase images are acquired from a magnetic resonance system with four channels, whereby images of water and fat can be reconstructed. Experimental results show that, when prior art reconstruction methods are used, errors often occur to reconstruction of a part of channels and reconstruction time is considerably long. The multi-channel magnetic resonance imaging reconstruction method for water-fat separation according to the present invention, however, can obtain correct images of water and fat in a relatively short time. FIG. 1A is an image showing water and fat of an embodiment; FIG. 1B is an image of the water of FIG. 1A obtained by employing the multi-channel magnetic resonance imaging reconstruction method for water-fat separation according to the present invention; and FIG. 1C is an image of the fat of FIG. 1A obtained by employing the multi-channel magnetic resonance imaging reconstruction method for water-fat separation according to the present invention.

Although modifications and changes may be suggested by those skilled in the art, it is the intention of the inventors to embody within the patent warranted hereon all changes and modifications as reasonably and properly come within the scope of their contribution to the art.

We claim:

1. A multi-channel magnetic resonance imaging reconstruction method for water-fat separation, comprising the steps of:

(i) acquiring one in-phase image and two opposed-phase images using multiple reception coils in respective channels of a magnetic resonance imaging;

(ii) calculating a sensitivity distribution of the coils of the respective channels;

(iii) merging the images of respective channels on the basis of the sensitivity distribution;

(iv) calculating a phase difference between the two opposed-phase images;

(v) detecting at least one characteristic region of the in-phase image, which is used as a criterion for phase correction; and (vi) correcting phases of the merged opposed-phase images and calculating images of water and fat therefrom.

2. A method as claimed in claim 1, wherein step (ii) further comprises calculating the sum of squares of moduli of the in-phase images of respective channels, which is then extracted:

$$SOS(x, y) = \sqrt{\sum_{i=1}^{n} |S_0^i(x, y)|^2},$$

wherein $S_0^i(x,y)$ is the in-phase image of channel i, i=1 . . . n, and n is the total number of the channels.

3. A method as claimed in claim 2, wherein step (ii) further comprises selecting a channel signal having a relatively high SNR $S_0^1(x,y)$ among the in-phase images and normalizing the modulus thereof:

$$S_0'(x, y) = \frac{S_0^I(x, y)}{|S_0^I(x, y)|}.$$

4. A method as claimed in claim 2, wherein step (ii) further comprises selecting a linear combination of respective channel signals and normalizing the modulus thereof:

$$S_0'(x, y) = \frac{\sum_{i=1}^{n} S_0^i(x, y) \cdot W_i}{\left|\sum_{i=1}^{n} S_0^i(x, y) \cdot W_i\right|},$$

wherein $W_i$ is a weighting.

5. A method as claimed in claims 3, wherein step (ii) further comprises calculating the sensitivity distribution of coils of respective channels as:

$$P^i(x, y) = \frac{S_0^i(x, y) \cdot [S_0'(x, y)]^*}{SOS(x, y)},$$

wherein [ ]* represents the conjugate.

6. A method as claimed in claim 1 comprising, in step (ii), utilizes a corrected space matched filter method to calculate the sensitivity distribution of coils of respective channels, wherein signals of each pixel and its neighborhood of images of respective channels are used to calculate the signal and noise correlation matrix, and the sensitivity distribution of coils of respective channels is derived by calculating the characteristic value and characteristic vector of the signal correlation matrix.

7. A method as claimed in claim 5 comprising, in said step (iii), merging the images of respective channels to obtain merged images having an optimized SNR, and at the same time, reserving phases of the images as:

$$S_0(x, y) = \sum_{i=1}^{n} [P^i(x, y)]^* \cdot S_0^i(x, y)$$

$$S_1(x, y) = \sum_{i=1}^{n} [P^i(x, y)]^* \cdot S_1^i(x, y)$$

$$S_2(x, y) = \sum_{i=1}^{n} [P^i(x, y)]^* \cdot S_2^i(x, y),$$

wherein $S_1^i(x,y)$ and $S_2^i(x,y)$ represent the two opposed-phased images, respectively.

8. A method as claimed in claim 7 comprising, in said step (iv), determining said phase difference between the two opposed-phase images is:

$$\phi(x,y) = \text{angle}[S_2(x,y) \cdot [S_1(x,y)]^*],$$

wherein angle[ ] represents the operator of calculating the phase angle.

9. A method as claimed in claim 8 comprising, using a phase unwrapping algorithm to perform phase unwrapping on said phase difference $\phi(x,y)$ to obtain a corrected phase $\phi'(x,y)$.

10. A method as claimed in claim 9 comprising, in step (v), detecting points in the fat signal and using said points as a criterion to correct said phase $\phi'(x,y)$.

11. A method as claimed in claim 9 comprising, in step (v), using an edge detection method detect points in the fat signal for subcutaneous fat, using said points as said criterion to correct said phase $\phi'(x,y)$.

12. A method as claimed in claim 9 comprising, in said step (vi), generating said images of water and fat as:

$$I_{water}(x,y) = 0.5 \cdot [S_0(x,y) + 0.5 \cdot (S_1(x,y) \cdot e^{j \cdot 0.5 \cdot \phi'(x,y)} + S_2(x,y) \cdot e^{-j \cdot 0.5 \cdot \phi'(x,y)})]$$

$$I_{fat}(x,y) = 0.5 \cdot [S_0(x,y) - 0.5 \cdot (S_1(x,y) \cdot e^{j \cdot 0.5 \cdot \phi'(x,y)} + S_2(x,y) \cdot e^{-j \cdot 0.5 \cdot \phi'(x,y)})]^*$$

* * * * *